United States Patent
Fujita et al.

(10) Patent No.: US 8,632,709 B2
(45) Date of Patent: Jan. 21, 2014

(54) PROCESS FOR PRODUCING WATER-DISPERSIBLE PARTICULATE AGRICULTURAL-CHEMICAL COMPOSITION

(75) Inventors: Shigeki Fujita, Tokyo (JP); Kazunori Kurita, Tokyo (JP)

(73) Assignees: Kumiai Chemical Industry Co., Ltd., Tokyo (JP); Nippon Soda Co., Ltd., Tokyo (JP)

( * ) Notice: Subject to any disclaimer, the term of this patent is extended or adjusted under 35 U.S.C. 154(b) by 188 days.

(21) Appl. No.: 13/132,032

(22) PCT Filed: Nov. 4, 2009

(86) PCT No.: PCT/JP2009/068793
§ 371 (c)(1),
(2), (4) Date: May 31, 2011

(87) PCT Pub. No.: WO2010/064513
PCT Pub. Date: Jun. 10, 2010

(65) Prior Publication Data
US 2011/0233812 A1    Sep. 29, 2011

(30) Foreign Application Priority Data
Dec. 1, 2008 (JP) ................................ 2008-306159

(51) Int. Cl.
*B29B 9/02* (2006.01)

(52) U.S. Cl.
USPC ............. 264/140; 264/15; 264/141; 264/142; 264/143; 264/144; 264/280; 264/340

(58) Field of Classification Search
USPC ........... 264/140, 141, 144, 15, 142, 143, 280, 264/340
See application file for complete search history.

(56) References Cited

U.S. PATENT DOCUMENTS

| | | | |
|---|---|---|---|
| 5,342,835 A * | 8/1994 | Pepin et al. | 514/227.5 |
| 5,925,380 A * | 7/1999 | Roulier et al. | 424/489 |
| 2006/0013846 A1 | 1/2006 | Kurita et al. | |
| 2006/0035787 A1 | 2/2006 | Dairiki et al. | |
| 2011/0039705 A1 | 2/2011 | Endo et al. | |

FOREIGN PATENT DOCUMENTS

| | | | |
|---|---|---|---|
| CA | 2722178 A1 * | 10/2009 | |
| CN | 1535579 A | 10/2004 | |
| CN | 1684584 A | 10/2005 | |
| CN | 1684586 A | 10/2005 | |
| EP | 1 552 743 A1 | 7/2005 | |
| EP | 1 559 319 A1 | 8/2005 | |
| EP | 2 269 452 A1 | 1/2011 | |
| JP | 7 75445 | 3/1995 | |
| JP | 2001 288004 | 10/2001 | |
| JP | 2003-40707 A | 2/2003 | |
| JP | 2003-95809 A | 4/2003 | |
| JP | 2004-26685 A | 1/2004 | |
| JP | 2005 194235 | 7/2005 | |
| JP | 2005 213197 | 8/2005 | |
| WO | 2008 152844 | 12/2008 | |
| WO | 2009 130910 | 10/2009 | |

OTHER PUBLICATIONS

Mospilan MSDS (http://www.nulandis.com/wp-content/uploads/2012/03/Mospilan-20-SP-msds1.pdf), retrieved Feb. 5, 2011.*
SGS Toothed Roll Crushers (http://www.sgs.com/~/media/Global/Documents/Flyers%20and%20Leaflets/SGS-MIN-WA025-Toothed-Roll-Crushers-EN-11.pdf), retrieved Feb. 5, 2011.*
Matsubo Roll Granulator (http://www.matsubo.co.jp/english/product/division/cat04/cat04_04/file070.html), retrieved Feb. 5, 2011.*
Edited by Pesticide Science Society of Japan. "Noyaku Seizai • Shiyoho Kenkyukai." Noyaku Saizai Guide. pp. 129-135 (1997).
International Search Report issued Dec. 28, 2009 in PCT/JP09/68793 filed Nov. 4, 2009.

* cited by examiner

*Primary Examiner* — Timothy Kennedy
(74) *Attorney, Agent, or Firm* — Oblon, Spivak, McClelland, Maier & Neustadt, L.L.P.

(57) ABSTRACT

A process for efficiently producing a water-dispersible particulate agricultural-chemical composition having improved disintegrability/dispersibility in water, the composition having a particular size in the range of 50-1,000 μm. The process is characterized by comprising the following steps (a) to (e): (a) a step of kneading an agricultural-chemical active ingredient, a surfactant, and water; (b) a step of extruding the resultant mixture through a screen having pores 600-2,000 μm in diameter to form granules; (c) a step of drying the granules; (d) a step of rotating two toothed rolls with irregularities on the surface arranged in parallel to each other, and leading the dried granules to pass between the toothed rolls thereby pulverizing the granules; and (e) a step of sieving the pulverized granules.

20 Claims, No Drawings

PROCESS FOR PRODUCING WATER-DISPERSIBLE PARTICULATE AGRICULTURAL-CHEMICAL COMPOSITION

TECHNICAL FIELD

The present invention relates to a process for producing a water-dispersible particulate agricultural-chemical composition for use in controlling pests and weeds for agricultural/horticultural crops.

BACKGROUND ART

Heretofore, various types of agricultural-chemical formulations such as dusts, granules, wettable powders, water-dispersible particulates, liquids, aqueous suspensions, emulsifiable concentrates, and the like have been known. Of these agricultural-chemical formulations, water-dispersible particulates are easy for users to handle since they do not powder during use thereof and therefore users would be exposed little to the agricultural-chemical ingredient and since they are easy to meter. Accordingly, forms of recent agricultural-chemical formulations tend to be changed from wettable powders to water-dispersible particulates.

In general water-dispersible particulates should easily disperse in water, and for this purpose they should be produced by a method in which granulation is not accompanied by application of pressure and the resulting granules are free from a consolidated structure. Such methods include a so-called fluidized-bed granulation method where a powdery mixture of an agricultural-chemical active ingredient, a surfactant and an extender or the like is fluidized in a layer into which hot air is pumped, and an aqueous solution containing a binder is sprayed thereon to make the powdery particles aggregate together thereby forming granules; and a so-called stirring granulation method where an aqueous solution containing a binder is sprayed on a powdery mixture of an agricultural-chemical active ingredient, a surfactant and an extender or the like kept stirred at high speed to make the powdery particles aggregate together thereby forming granules (Non-Patent Documents 1 and 2).

In these methods, however, the granules produced have a broad particle size distribution and sieving results in a low production yield with respect to a necessary particle size. In addition, since the granulation is carried out as a batch process, the amount of the granules to be produced per unit time is small. Therefore, the methods are substantially unsuitable for industrial production of agricultural chemicals.

On the other hand, as a granulation method that secures high producibility of agricultural-chemical formulations, there is a so-called extrusion granulation method where an agricultural-chemical active ingredient, a surfactant and an extender or the like are kneaded with water, and extruded through pores formed in a screen to give columnar granules (Non-Patent Document 1). In this method, a high pressure is given to extrude the mixture through the pores and, as a result, the formed granules have a consolidated structure with poor water-dispersibility. In this connection, while the water-dispersibility could be improved by reducing the diameter of the pores to have smaller granules, the pressure to be imparted to the screen may increase with reduction in the diameter of the pores and cause increased fragility of the screen thereby precluding the granulation itself.

Also, as a method for producing a granular agricultural-chemical composition having improved water-dispersibility and suspensibility of agricultural-chemical ingredient, there is a method in which a mixture containing an agricultural-chemical active ingredient and a surfactant is kneaded with water, and the kneaded mixture is pulverized to have a predetermined particle size and dried, or the kneaded mixture is dried and made to have a predetermined particle size (Patent Document 1). In this method, although the resulting granules are not in a consolidated state and have good water-dispersibility, the step of pulverizing the kneaded mixture may cause problems. Specifically, in the case where the kneaded mixture before dried is pulverized, the mixture significantly adheres to the pulverizer because of water contained in the mixture. On the other hand, the kneaded mixture which is dried before the pulverization is extremely brittle and the size distribution of the pulverized particles is large, therefore the production yield of the granular agricultural-chemical composition having the intended particle size is extremely low.

Patent Document 1: JP-A 2001-288004
Non-Patent Document 1: Handbook of Granulation Technology, edited by the Association of Power Process Industry and Engineering, Japan
Non-Patent Document 2: Granulation Manual, edited by the Association of Power Process Industry and Engineering, Japan

DISCLOSURE OF INVENTION

Problem to be Solved by the Invention

Accordingly, an object of the invention is to provide a method for efficient production of a water-dispersible particulate agricultural-chemical composition having improved disintegrability/dispersibility in water.

Means for Solving the Problems

The present inventors have assiduously studied methods for producing granular agricultural-chemical composition and, as a result, have found that a water-dispersible particulate agricultural-chemical composition having a desired particle size range can be extremely efficiently obtained by producing granules according to an extrusion granulation method using a screen having pores slightly larger in diameter than the desired particle size, drying and pulverizing the granules so as not to powder, and further sieving the pulverized particles to have a desired particle size. Thus, the present invention was completed.

Specifically, the present invention may be summarized as follows.

(1) A method for producing a water-dispersible particulate agricultural-chemical composition having a particle size within a range of from 50 to 1,000 μm, the method comprises the following steps (a) to (e):
 (a) a step of kneading an agricultural-chemical active ingredient, a surfactant and water,
 (b) a step of extruding the kneaded mixture through a screen having pores from 600 to 2,000 μm in diameter to form granules,
 (c) a step of drying the granules,
 (d) a step of rotating two toothed rolls with irregularities on the surface arranged in parallel to each other, and leading the dried granules to pass through the toothed rolls thereby pulverizing the granules, and
 (e) a step of sieving the pulverized particles.

(2) The method for producing a water-dispersible particulate agricultural-chemical composition of the above (1), wherein in the step (e), the pulverized particles are sieved through two (3) The method for producing a water-dispersible particulate agricultural-chemical composition of the above (2), wherein in the step (e), the pulverized particles are sieved in such a manner that the particles are first sieved through the mesh having the larger opening diameter of the two types of meshes each having an opening diameter within a range of from 50 to 1,000 μm, then those having passed through the sieve are further sieved through the mesh having the smaller opening diameter, and those having remained on the mesh are collected.

Effect of the Invention

In the method for producing a water-dispersible particulate agricultural-chemical composition of the present invention, the material loss in the production process is low and the load to the machines for the production is also low. In addition, the production yield of the water-dispersible particulate agricultural-chemical composition having the intended particle size is high compared with that in conventional production methods.

Accordingly, the method of the present invention is an extremely efficient and economical method for producing a water-dispersible particulate agricultural-chemical composition.

BEST MODE FOR CARRYING OUT THE INVENTION

The term "particle size" as used herein, means the range in which the diameter of the individual particles in the water-dispersible particulate agricultural-chemical composition falls. For example, a water-dispersible particulate agricultural-chemical composition having a particle size of from 250 to 500 μm means the particles which have passed through a mesh having an opening diameter of 500 μm and remain on a mesh having an opening diameter of 250 μm, that is, the composition in which the diameter of all the particles falls within a range of from 250 to 500 μm.

The method of the present invention for producing a water-dispersible particulate agricultural-chemical composition having a particle size within a range of from 50 to 1,000 μm (hereinafter referred to as "the method of the invention") is characterized by comprising the following steps (a) to (e):
(a) a step of kneading an agricultural-chemical active ingredient, a surfactant and water,
(b) a step of extruding the kneaded mixture through a screen having pores from 600 to 2,000 μm in diameter to form granules,
(c) a step of drying the granules,
(d) a step of rotating two toothed rolls with irregularities on the surface arranged in parallel to each other, and leading the dried granules to pass through the toothed rolls thereby pulverizing the granules, and
(e) a step of sieving the pulverized particles.

The step (a) in the method of the invention is a step of kneading an agricultural-chemical active ingredient, a surfactant and optionally any other ingredient and water. In this step, the above-mentioned ingredients are uniformly mixed, thereby enabling efficient granulation in the next step (b). Apparatuses for use in the kneading include a Henschel mixer, a twin-arm kneader, a paddle mixer, a blade mixer, a high-speed mixer, a vertical mixer, and the like. The amount of water in kneading may be adjusted to a level suitable for extrusion granulation, and may be from 5 to 30 parts, preferably from 10 to 20 parts relative to the total amount, 100 parts of the above-mentioned agricultural-chemical active ingredient, surfactant and any other optional ingredient.

Prior to being kneaded with water, preferably, the agricultural-chemical active ingredient, the surfactant and the others are mixed and optionally these ingredients are ground into powdery particles having a uniform particle size, using a grinder as typified by an impact grinder, a high-speed airflow-assisted grinder or the like. The mean particle diameter of the ground powdery particles is from 1 to 20 μm, preferably from 1 to 15 μm, more preferably from 2 to 10 μM. The term "mean particle diameter" as referred to herein, means a volume median diameter.

The agricultural-chemical active ingredients include those known in the agricultural-chemical field, such as insecticides, microbicides, herbicides, plant growth regulators, and the like. The agricultural-chemical active ingredients may be in any form of liquid, solid or paste, including the following examples, to which, however, the invention should not be limited.

Specific examples of insecticides include acrinathrin, acetamiprid, acephate, amitraz, alanycarb, arimarua, alumigelure, isoxathion, imidacloprid, indoxacarb MP, uwabarua, ethylthiometon, etoxazole, etofenprox, emamectin benzoate, oxamyl, orifurua, sodium oleate, carbam ammonium salt, carbam sodium salt, cadusafos, cartap hydrochloride, carbosulfan, clothianidin, clofentezine, chromafenozide, chloropicrin, chlorpyrifos, chlorpyrifos-methyl, chlorfenapyr, chlorfluazuron, diatomaceous earth, fenbutatin oxide, dienochlor, cycloprothrin, dinotefuran, cyhalothrin, cyfluthrin, diflubenzuron, cypermethrin, fatty acid glycerides, dimethoate, methyl bromide, silafluofen, cyromazine, spinosad, spirodiclofen, sulprofos, diazinon, diamolure, thiacloprid, thiamethoxam, thiodicarb, thiocyclam, thiometon, cheritoria, tetradifon, tetradecenyl acetate, tebufenozide, tebufenpyrad, tefluthrin, teflubenzuron, tralomethrin, tolfenpyrad, nitenpyram, pasteuria penetrans, halfenprox, peachflure, pitoamirua, bifenazate, bifenthrin, pymetrozine, pyraclofos, pyridaphenthion, pyridaben, pyridalyl, pirimarua, pyrimidifen, pirimiphos-methyl, pyrethrin, fipronil, fenothiocarb, fenvalerate, fenpyroximate, fenpropathrin, buprofezin, furathiocarb, fluacrypyrim, flucythrinate, fluvalinate, flufenoxuron, prothiofos, propaphos, propylene glycol fatty acid esters, profenofos, hexythiazox, permethrin, bensultap, benzoepin, benfuracarb, phosalone, fosthiazate, machine oil, marathon, milbemectin, methomyl, metaldehyde, methyl isothiocyanate, methoxyfenozide, litlure, lufenuron, rotenone (derris), BPMC, BPPS, BRP, BT, CYAP, D-D, DCIP, DDVP, DEP, DMTP, ECP, EPN, MEP, MPP, NAC, PAP, XMC, ethiprole. Ethofenprox is preferred among these insecticides.

Specific examples of microbicides include azoxystrobin, amobam, sulfur, isoprothiolane, ipconazole, iprodione, iminoctadine albesilate, iminoctadine acetate, imibenconazole, echlomezole, oxadixyl, oxytetracycline, oxpoconazole fumarate, oxolinic acid, kasugamycin, carpropamid, quinoxalines, captan, kresoxim-methyl, cyazofamid, shiitake mushroom mycelium extract, diethofencarb, diclocymet, diclomezine, dithianon, difenoconazole, cyproconazole, cyflufenamid, cyprodinil, simeconazole, dimethomorph, cymoxanil, *Pseudomonas* bacteria CAB-02, ziram, streptomycin, lime sulfur mixture, dazomet, potassium bicarbonate, sodium bicarbonate, thiadiazine, tiadinil, thiabendazole, thiuram, thiophanate-methyl, thifluzamide, tecloftalam, tebuconazole, tetraconazole, basic copper chloride, basic copper sulfate, cupric hydroxide, triadimefon, triazine, *trichoderma atroviride* SKT-1, tricyclazole, triflumizole, trifloxystrobin, triforine, tolclofos-methyl, rapeseed oil, copper nonylphenolsulfonate, *Bacillus subtilis* bacteria (living cells), validamycin, bitertanol, hydroxyisoxazole, non-pathogenic *Erwinia carotovora*, pyrifenox, pyribencarb, pyroquilon, famoxadone, fenarimol, fenoxanil, ferimzone, fenbuconazole, fenhexamid, fthalide, Blasticidin S, furametpyr, fluazinam, fluoroimide, fludioxonil, flusulfamide, flutolanil, prochloraz, procymidone, propamocarb hydrochloride, propiconazole, propineb, probenazole, hexaconazole, benomyl, pefurazoate, pencycuron, benthiavalicarb-isopropyl, fosetyl, polyoxin, polycarbamate, manzeb, maneb, mildiomycin, anhydrous copper sulfate, metalaxyl, metominostrobin, mepanipyrim, mepronil, organocopper, DBEDC, EDDP, IBP, TPN, boscalid, and the like. Pyribencarb, benthiavalicarb-isopropyl, iminoctadine albesilate, mepanipyrim and mepronil are preferred among these microbicides.

Specific examples of herbicides include ioxynil, azimsulfuron, asulam, atrazine, anilofos, alachlor, isoxaben, isouron, imazamox ammonium salt, imazosulfuron, indanofan, esprocarb, ethoxysulfuron, etobenzanide, chlorates, oxadiazon, oxaziclomefone, cafenstrole, karbutilate, quizalofop-ethyl, cumyluron, glyphosate ammonium salt, glyphosate isopropylamine salt, glyphosate trimesium salt, glyphosate sodium salt, glufosinate, clethodim, clomeprop, cyanazine, sodium cyanate, cyclosulfamuron, diquat dibromide, siduron, cyhalofop butyl, diflufenican, dimethametryn, dimethenamid, simetryne, dimepiperate, sethoxydim, terbacil, dymron, thifensulfuron-methyl, desmedipham, thenylchlor, tebuthiuron, tepraloxydim, trifluralin, nicosulfuron, paraquat, halosulfuron-methyl, bialaphos, bispyribac sodium salt, bifenox, pyrazoxyfen, pyrazosulfuron-ethyl, pyrazolate, pyraflufenethyl, pyriftalid, pyributicarb, pyrimisulfan, pyriminobac-methyl, pyroxasulfone, fenoxaprop-ethyl, fentrazamide, phenmedipham, butachlor, butamifos, flazasulfuron, fluazifop P, pretilachlor, bromacil, prometryn, bromobutide, bensulfuron-methyl, benzobicyclon, benzofenap, bentazone, benthiocarb, pendimethalin, pentoxazone, benfuresate, metamitron, metolachlor, metribuzin, mefenacet, molinate, linuron, lenacil, 2,4 PA, ACN, CAT, DBN, DCMU, DCPA, DPA, IPC, MCPA ethyl, MCPA thioethyl, MCPA sodium salt, MCPB, MDBA, PAC, SAP, and isoxazoline derivatives represented by a formula [I]:

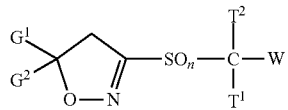

[I]

[wherein n indicates an integer of from 0 to 2; $T^1$ and $T^2$ each independently represent a hydrogen atom, a halogen atom, a cyano group, a lower alkoxycarbonyl group, or a $C_1$-$C_6$ alkyl group; $G^1$ and $G^2$ each independently represent a hydrogen atom, a $C_1$-$C_6$ alkyl group, or a $C_1$-$C_6$ haloalkyl group; W represents a phenyl group (substituted with from 1 to 5 and the same or different V's); V represents a hydrogen atom, a $C_1$-$C_6$ alkyl group {optionally substituted with from 1 to 3 and the same or different substituents of a halogen atom, a $C_1$-$C_6$ alkoxy group, a hydroxyl group, a $C_1$-$C_6$ alkylthio group, a $C_1$-$C_6$ alkylsulfinyl group, a $C_1$-$C_6$ alkylsulfonyl group, a $C_1$-$C_6$ alkylamino group, a $C_1$-$C_6$ dialkylamino group, a cyano group or a phenoxy group (optionally substituted)}, a $C_1$-$C_6$ alkoxy group (optionally substituted with from 1 to 3 and the same or different substituents of a halogen atom, a $C_1$-$C_6$ alkoxy group, a $C_2$-$C_6$ alkenyl group, a $C_2$-$C_6$ alkynyl group, a $C_1$-$C_6$ alkoxycarbonyl group, a $C_1$-$C_6$ alkylcarbonyl group or a $C_3$-$C_8$ cycloalkyl group), a $C_3$-$C_8$ cycloalkyloxy group, or a halogen atom].

Pyriminobac-methyl, pyrimisulfan, pyroxasulfone and isoxazoline derivatives of formula [I] are preferred among these herbicides.

Specific examples of plant growth regulators include 1-naphthylacetamide, inabenfide, indole butyric acid, uniconazole P, ethyclozate, ethephon, calcium peroxide, cloxyfonac, chlormequat, choline, dichlorprop, gibberellin, daminozide, decyl alcohol, paclobutrazol, prohexadione-calcium, benzylaminopurine, forchlorfenuron, mepiquat-chloride, 4-CPA, and the like.

These agricultural-chemical active ingredients may be used singly, or two or more different types thereof may be used in combination depending on the pests and the weeds to be controlled and the crops to be protected. The total content of the agricultural-chemical active ingredients in the water-dispersible particulate agricultural-chemical composition to be produced according to the method of the invention is not specifically defined, and may be approximately from 1 to 85 parts by weight relative to 100 parts by weight of the composition.

As the surfactant, nonionic surfactants, anionic surfactants, cationic surfactants, ampholytic surfactants, and the like may be used with no limitation. Examples of those types of surfactants are mentioned below, to which, however, the invention should not be limited.

Specific examples of nonionic surfactants include polyoxyalkylene glycols, polyoxyalkylene alkyl ethers, polyoxyalkylene alkyl aryl ethers, polyoxyalkylene fatty acid esters, polyoxyethylene-polyoxypropylene block polymers, sorbitan monoalkylates, alkynols and alkynediols, as well as alkylene oxide adducts thereof.

Specific examples of anionic surfactants include alkali metal salts, alkaline earth metal salts or ammonium salts of alkyl sulfuric acids, alkyl sulfonic acids, alkyl phosphoric acids, alkyl phosphonic acids, alkylaryl sulfonic acids, alkylaryl phosphonic acids, polyoxyalkylene alkyl ether sulfate esters, polyoxyalkylene alkylaryl ether sulfate esters, polyoxyalkylene alkyl ether phosphate esters, polyoxyalkylene alkylaryl ether phosphate esters, polycarboxylic acid-type polymers, lignin sulfonic acids, aryl sulfonic acids, aryl sulfonic acid-formalin condensates, alkylaryl sulfonic acid-formalin condensates, and the like. Salts of alkyl sulfuric acids, alkylaryl sulfonic acids, polycarboxylic acids, lignin sulfonic acids, aryl sulfonic acids, or arylsulfonic acid-formalin condensates are preferred among these anionic surfactants.

Specific examples of cationic surfactants include hydrochlorides, sulfates or carboxylates of alkylamines, polyalkylamines, alkanolamines, polyalkanolamines, polyalkylenepolyamines, alkylpyridines, alkylmorpholines, alkylhydrazines, and the like.

These surfactants may be used singly, or two or more different types thereof may be used in combination. The total content of the surfactants in the water-dispersible particulate agricultural-chemical composition to be produced according to the method of the invention is not specifically defined, and may be approximately from 2 to 30 parts by weight relative to 100 parts by weight of the composition.

Other ingredients that may be optionally added to the above-mentioned agricultural-chemical active ingredient, surfactant and water include those that may be used in ordinary water-dispersible agricultural-chemical composition. For example, formulation additives such as water-soluble fine powder, mineral fine powder, oil-absorbing fine powder, binder, grinding aid, defoaming agent and the like may be optionally incorporated. The water-soluble fine powder includes lactose, water-soluble starch, urea, alkali metal salts or ammonium salts of organic acids or inorganic acids, and the like. The mineral fine powder includes diatomaceous earth, clay, calcium carbonate, and the like. The oil-absorbing fine powder includes white carbon, diatomaceous earth, microcrystalline cellulose, and the like. The binder includes polyvinyl alcohol, carboxymethyl cellulose, hydroxypropyl cellulose, and the like. The grinding aid includes white carbon, silica sand, pumice, and the like. The defoaming agent is not specifically defined, and may include silicone-based surfactants, free long-chain fatty acids or alkali metal salts thereof, and the like.

The mixture kneaded in the above-mentioned step is then extruded through a screen having pores from 600 to 2,000 μm in diameter to form granules in the next step (b). The pore size of the screen is preferably from 600 to 1,800 μm, more preferably from 600 to 1,500 μm. In cases where the pore size of the screen is smaller than the range, not only does the yield per unit time in extrusion granulation extremely decline but the pressure in passing through the screen increases, leading to increased frequency of screen breakage. On the other hand, when the pore size is larger than the range, the granulation yield per unit time could be large but the efficiency may be undermined because more time is required for drying and the production yield in the step (d) may be decline with increase in unintended fine powder in grinding. The pore size of the screen is preferably from 0.6 to 3 times, more preferably from 0.8 to 2 times the larger opening diameter of the meshes for use in sieving in the step (e).

Any granulator can be used for extrusion granulation as long as the machine is equipped for granulation, and its shape is not specifically defined. Specific examples of the granulator include a horizontal extrusion-type screw-extrusion granulator, a disc die-type roll-extrusion granulator, a basket-type blade-extrusion granulator, and the like.

The granules formed as above are then dried in the step (c). Using a drier such as a fluidized bed drier or the like, the granules are dried at a hot air temperature of from 50 to 100° C. or so for 10 to 20 minutes or so. In the operation, the intralayer temperature in the granules rises to the same level as that of the hot air temperature and the water content thereof decreases generally to 0.5 to 3% by mass. When not dried, the granules may be again kneaded together by the rotational movement of the pulverizer in the next step (d) and therefore the granules could not be pulverized.

The granules obtained in the above-mentioned step are in the form of columns having a constant size, having each of the ingredients uniformly dispersed therein, and are in a consolidated state (a strongly-compacted state having a uniform density).

The granules are then subjected to the step (d). In the step, two toothed rolls with irregularities formed on the surface are arranged in parallel to each other with a predetermined distance, and these toothed rolls are rotated. Then the dried granules are led to pass through the rotating rolls for pulverization. Through this step, the pulverized particles comprising a lot of granules of a desired particle size can be obtained to enable efficient production of the water-dispersible particulate agricultural-chemical composition having a desired particle size range. In this step, preferably, the toothed rolls are arranged in parallel to the ground and the dried granules are thrown from above into the toothed rolls.

The toothed rolls for use in this step each have irregularities formed on the roll surface. In general, the diameter of the roll is from 50 mm to 300 mm and the length thereof is from 20 mm to 1,500 mm. The shape of the irregularities of the toothed rolls is not specifically defined. Preferably, the cross section of the irregularities has a profile of continuous triangular mounds. The shape of the triangles is not also specifically defined. Preferably, the height and the width (base) of the triangle fall within a range of from 0.3 mm to 10 mm and more preferably, the height and the width are the same. Further, the distance between the rolls is not specifically defined, and in general, it may be from 0.05 mm to 1.5 mm. The size of the pulverized particles can be controlled by changing the shape of the teeth of the rolls and the distance between the rolls. In general, when the height and the width of the triangles of the teeth are narrower, and when the distance between the rolls is narrower, the pulverized particles may be smaller. The apparatus for such pulverizing may be a frame-type pulverizing apparatus.

In the present invention, the particles pulverized as in the above may be further pulverized by using two or more of the above-mentioned pair of two toothed rolls in combination. In this case, preferably, the shape of the teeth of the rolls and the distance between the rolls are so configured that the latter pulverizing could give particles having a smaller particle size than the first pulverizing. A combination of these toothed rolls comprises, for example, rolls with triangle teeth having a height and a width of 1 mm each, arranged at the distance of 0.27 mm for the first pulverization; and rolls with triangle teeth having a height and a width of 0.6 mm each, arranged at the distance of 0.25 mm for the latter pulverization.

The particles pulverized as in the above are then sieved in the step (e). The sieving is conducted to obtain the water-dispersible particulate agricultural-chemical composition having a particle size within a range of from 50 to 1,000 μm, preferably from 100 to 850 μm, more preferably from 250 to 700 μm. Concretely, the sieving may be attained by the use of two types of meshes each having an opening diameter within a range of from 50 to 1,000 μm. More concretely, the pulverized particles are first sieved through the mesh having the larger opening diameter of the two types of meshes each having an opening diameter within a range of from 50 to 1,000 μm, then the particles having passed through the sieve are further sieved through the mesh having the smaller opening diameter, and those having remained on the mesh are collected. For example, the water-dispersible particulate agricultural-chemical composition having a particle size of from 250 to 600 μm can be obtained by first sieving the pulverized particles through a mesh having an opening diameter of 600 μm, then further sieving those having passed through it, through a mesh having an opening diameter of 250 μm, and collecting those having remained on the mesh. The machine for the sieving includes a rotary shifter, a shaking sieve, and the like.

According to the steps (a) to (e) described above, the water-dispersible particulate agricultural-chemical composition having a particle size of from 50 to 1,000 μm can be produced efficiently.

The water-dispersible particulate agricultural-chemical composition thus produced is excellent in disintegrability/dispersibility in water.

In the present invention, the reason why the water-dispersible particulate agricultural-chemical composition having a particle size of from 50 to 1,000 μm can be produced efficiently is because a uniform kneaded mixture of ingredients such as an agricultural-chemical active ingredient and others is produced in the step (a), and then granules having a shape of columns with a constant size in a consolidated state are produced in the step (b). In addition, when the granules dried in the step (c) are led to pass through two toothed rolls used in the latter-stage of the step (d), almost all the granules are cut from the side of each column to be pulverized since the granules have a shape of columns with a constant size; and while they are pulverized, the consolidated structure of the granules prevents generation of large amount of unintended fine powder, with the result that the water-dispersible particulate agricultural-chemical composition having a desired particle size can be obtained efficiently in a high production yield.

On the other hand, when the ingredients of the granules to be processed in the step (d) are not homogeneous, when the density of the granules is not uniform, or when the granules are amorphous, then the particles pulverized in the step (d) have a broad particle size distribution, and in particular, unintended fine particles are formed much, resulting in a low production yield.

EXAMPLES

The present invention will be described in more detail with reference to Examples and Comparative Examples; however, the invention should not be limited to these Examples. In the following Examples, the term "part" means part by weight.

Example 1

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 800 μm in diameter. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 500 μm, and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Example 2

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 1,800 μm in diameter. The obtained granules were dried in a fluidized bed drier at a hot air temperature of 55° C. for about 20 minutes until the intralayer temperature could reach 55° C. Subsequently, using a frame-type pulverizing apparatus having two pairs of toothed rolls arranged one above the other in parallel to the ground and having a slot above the rolls, the dried granules were led to pass through the rotating rolls in this apparatus and pulverized. The height and the width of the triangles of the teeth were both 1.5 mm and the distance between the rolls was 0.8 mm in the upper pair of rolls; and the height and the width were both 0.6 mm and the distance was 0.25 mm in the lower pair of rolls. The pulverized particles were then sieved through a mesh having an opening diameter of 500 μm, and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Example 3

40 parts of mepanipyrim, 2 parts of sodium alkyl sulfate, 8 parts of sodium lignin sulfonate, and 50 parts of clay were mixed, and ground with a high-speed airflow-assisted grinder so that the mean particle size of the ingredients could be 5 μm. Next, 18 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 1,000 μm in diameter. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 600 μm, and those having passed through the mesh were further sieved through a mesh having an opening diameter of 150 μm; and those having remained on the mesh were collected to obtain a water-dispersible particulate agricultural-chemical composition having a particle size within a range of from 150 to 600 μm.

Example 4

10 parts of pyribencarb, 30 parts of a mixture (1/1 by weight) of iminoctadine albesilate and white carbon, 4 parts of sodium alkyl sulfate, 15 parts of maleic anhydride-isobutylene copolycondensate, and 41 parts of calcium carbonate were mixed, and ground with a high-speed airflow-assisted grinder so that the mean particle size of the ingredients could be 9 μm. Next, 20 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 600 μm in diameter. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 600 μm, and those having passed through the mesh were further sieved through a mesh having an opening diameter of 150 μm; and those having remained on the mesh were collected to obtain a water-dispersible particulate agricultural-chemical composition having a particle size within a range of from 150 to 600 μm.

Example 5

50 parts of pyriminobac-methyl, 20 parts of sodium alkylnaphthalene sulfonate-formalin condensate, 1 part of polyoxyalkylene alkylaryl ether, and 29 parts of calcined diatomaceous earth were mixed, and ground with a high-speed airflow-assisted grinder so that the mean particle size of the ingredients could be 4 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 700 μm in diameter. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 500 and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Example 6

85 parts of pyroxasulfone, 3 parts of sodium alkylnaphthalene sulfonate-formalin condensate, 8 parts of sodium lignin sulfonate, 1 part of polyoxyalkylene aryl ether, and 3 parts of calcined diatomaceous earth were mixed, and ground with a high-speed airflow-assisted grinder so that the mean particle size of the ingredients could be 5 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 800 μm in diameter. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 500 μm, and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Comparative Example 1

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pore 300 μm in diameter. However, since the screen was broken and the granulation could not be attained, the intended water-dispersible particulate agricultural-chemical composition could not be obtained.

Comparative Example 2

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, 15 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 3,000 μm in diameter. The obtained granules were dried in a fluidized bed drier at a hot air temperature of 55° C. for about 20 minutes until the intralayer temperature could reach 55° C. Subsequently, using a frame-type pulverizing apparatus having three pairs of toothed rolls arranged in upper, middle and lower three stages so as to be in parallel to the ground and having a slot above the rolls, the dried granules were led to pass through the rotating rolls in this apparatus and pulverized. The height and the width of the triangles of the teeth were both 2.0 mm and the distance between the rolls was 1.5 mm in the upper pair of rolls; the height and the width were both 1.5 mm and the distance was 0.8 mm in the middle pair of rolls; and the height and the width were both 0.6 mm and the distance was 0.25 mm in the lower pair of rolls. The pulverized particles were then sieved through a mesh having an opening diameter of 500 μm, and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Comparative Example 3

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, with spraying 15 parts of water onto 100 parts of the ground particles, granules having a particle size of from 100 to 5,000 μm or so were obtained by means of a stirring granulator. The obtained granules were dried in a fluidized bed drier at a hot air temperature of 55° C. for about 10 minutes until the intralayer temperature could reach 55° C. Subsequently, using a frame-type pulverizing apparatus having two toothed rolls arranged in parallel to the ground and having a slot above the rolls, the dried granules were led to pass through the rotating rolls in this apparatus and pulverized. The height and the width of the triangles of the teeth were both 0.6 mm and the distance between the rolls was 0.25 mm. The pulverized particles were then sieved through a mesh having an opening diameter of 500 μm, and those having passed through the mesh were further sieved through a mesh having an opening diameter of 250 μm; and those having remained on the mesh were collected to obtain a water-dispersible particulate agricultural-chemical composition having a particle size within a range of from 250 to 500 μm.

Comparative Example 4

40 parts of pyribencarb, 4 parts of sodium alkyl sulfate, 5 parts of sodium lignin sulfonate, and 51 parts of calcium carbonate were mixed, and ground with a high-speed airflow-assisted grinder so that the mean particle size of the ingredients could be 7 μm. Next, with spraying 15 parts of water onto 100 parts of the ground particles, granules having a particle size of from 100 to 5,000 μm or so were obtained by means of a stirring granulator. Using a frame-type pulverizing apparatus having two toothed rolls arranged in parallel to the ground and having a slot above the rolls, the obtained granules were, without being dried, led to pass through the rotating rolls in this apparatus so as to be pulverized. However, since the granules were again kneaded together between the rolls and could not be pulverized, the intended water-dispersible particulate agricultural-chemical composition could not be obtained. The height and the width of the triangles of the teeth were both 0.6 mm and the distance between the rolls was 0.25 mm.

Comparative Example 5

10 parts of pyribencarb, 30 parts of a mixture (1/1 by weight) of iminoctadine albesilate and white carbon, 4 parts of sodium alkyl sulfate, 15 parts of sodium naphthalene-sulfonate-formaldehyde condensate, and 41 parts of calcium carbonate were mixed, and ground with a high-speed airflow-assisted grinder so that the mean particle size of the ingredients could be 9 μm. Next, 20 parts of water was added to 100 parts of the ground particles, and further kneaded. At the time when the added water had penetrated into the whole mixture, the kneaded mixture was granulated with a horizontal extrusion-type screw-extrusion granulator. The screen used in extrusion granulation had pores 600 μm in diameter. The obtained granules were dried in a fluidized bed drier at a hot air temperature of 55° C. for about 10 minutes until the intralayer temperature could reach 55° C. The dried granules were sieved through a mesh having an opening diameter of 600 μm, and those having passed through the mesh were further sieved through a mesh having an opening diameter of 150 μm; and those having remained on the mesh were collected to obtain a water-dispersible particulate agricultural-chemical composition having a particle size within a range of from 150 to 600 μm.

Test Example 1

Disintegration Test 0.3077 g of calcium carbonate and 0.092 g of magnesium oxide were dissolved in a small amount of diluted hydrochloric acid, then heated and boiled on a sand bath to remove hydrochloric acid. Distilled water was added to the remaining solution to make 10 liters in total. Subsequently, 100 ml of the obtained solution was put into a 100-ml stoppered measuring cylinder, and kept at 20° C. in a temperature-controlled room. 100 mg of the water-dispersible particulate agricultural-chemical composition produced in Examples 1 to 6 and Comparative Example 5 was put into the measuring cylinder, statically left as it was for 30 seconds, and then the measuring cylinder was turned upside down repeatedly in a ratio of once a second, whereupon the turning-down frequency needed for disintegrating the whole water-dispersible particulate agricultural-chemical composition was counted. The results are shown in Table 1.

TABLE 1

| Formulation Example | Turning-down Frequency needed for disintegration |
|---|---|
| Example 1 | 5 |
| Example 2 | 5 |
| Example 3 | 4 |
| Example 4 | 8 |
| Example 5 | 10 |
| Example 6 | 7 |
| Comparative Example 5 | at least 50 |

From Table 1, it is known that the water-dispersible particulate agricultural-chemical compositions of the present invention have high disintegrability in water and are excellent in dispersibility.

Test Example 2

Evaluation of Production Efficiency

Using starting materials of 10 kg in total, water-dispersible particulate agricultural-chemical compositions were produced according to the above-mentioned Examples and Comparative Examples, and the weight of the finally-obtained water-dispersible particulate agricultural-chemical composition was measured. The results are shown in Table 2.

TABLE 2

| | Weight of Water-dispersible Particulate Agricultural-Chemical Composition produced from 10 kg of starting materials |
|---|---|
| Example 1 | 7.9 kg |
| Example 2 | 7.5 kg |
| Example 3 | 7.4 kg |
| Example 4 | 9.3 kg |
| Example 5 | 8.5 kg |
| Example 6 | 8.3 kg |
| Comparative Example 2 | 5.5 kg |
| Comparative Example 3 | 3.6 kg |

From Table 2, it is known that the method for producing a water-dispersible particulate agricultural-chemical composition of the present invention provides a high production yield and is excellent in production efficiency.

INDUSTRIAL APPLICABILITY

According to the method for producing a water-dispersible particulate agricultural-chemical composition of the present invention, a loss of starting materials in the production process is small, a load to the machine for the production is low, and the production yield of the water-dispersible particulate agricultural-chemical composition having a desired particle size is high as compared with conventional production methods.

Therefore, the method of the present invention can be advantageously used in producing a water-dispersible particulate agricultural-chemical composition for use in controlling pests and weeds for agricultural/horticultural crops.

The invention claimed is:

1. A method for producing a water-dispersible particulate composition, the method comprising:
   (a) kneading an active ingredient, a surfactant and water to form a kneaded mixture,
   (b) extruding the kneaded mixture through a screen having pores from 600 to 2,000 μm in diameter to form granules,
   (c) drying the granules to form dried granules,
   (d) rotating two toothed rolls with irregularities on their surfaces, arranged in parallel to each other, such that the dried granules pass through the toothed rolls to form pulverized particles, and
   (e) sieving the pulverized particles,
   wherein the water-dispersible particulate composition has a particle size within a range from 50 to 1,000 μm.

2. The method of claim 1, wherein the sieving (e) of the pulverized particles occurs through two types of meshes each having an opening diameter within a range of from 50 to 1,000 μm.

3. The method of claim 2, wherein:
   the sieving (e) of the pulverized particles occurs first through a mesh having the larger opening diameter of the two types of meshes,
   the pulverized particles, which passed through the larger opening diameter sieve, are further passed through a mesh having a smaller opening diameter, and
   the pulverized particles remaining on the smaller opening diameter mesh are collected.

4. The method of claim 1, wherein the active ingredient is an agricultural chemical composition.

5. The method of claim 1, wherein the active ingredient is at least one selected from the group consisting of etofenprox, pyribencarb, benthiavalicarb-isopropyl, iminoctadine albesilate, mepanipyrim, mepronil, pyriminobac-methyl, pyrimisulfan, pyroxasulfone, and isoxazoline derivatives of formula [I]

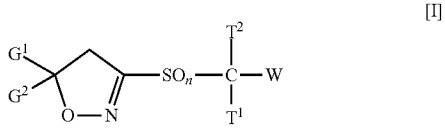

wherein n indicates an integer of from 0 to 2; $T^1$ and $T^2$ each independently represent a hydrogen atom, a halogen atom, a cyano group, a lower alkoxycarbonyl group, or a $C_1$-$C_6$ alkyl group; $G^1$ and $G^2$ each independently represent a hydrogen atom, a $C_1$-$C_6$ alkyl group, or a $C_1$-$C_6$ haloalkyl group; and W represents a phenyl group substituted with from 1 to 5 and the same or different V's; V represents a hydrogen atom, a $C_1$-$C_6$ alkyl group optionally substituted with from 1 to 3 and the same or different substituents of a halogen atom, a $C_1$-$C_6$ alkoxy group, a hydroxyl group, a $C_1$-$C_6$ alkylthio group, a $C_1$-$C_6$ alkylsulfinyl group, a $C_1$-$C_6$ alkylsulfonyl group, a $C_1$-$C_6$ alkylamino group, a $C_1$-$C_6$ dialkylamino group, a cyano group or a phenoxy group optionally substituted, a $C_1$-$C_6$ alkoxy group optionally substituted with from 1 to 3 and the same or different substituents of a halogen atom, a $C_1$-$C_6$ alkoxy group, a $C_2$-$C_6$ alkenyl group, a $C_2$-$C_6$ alkynyl group, a $C_1$-$C_6$ alkoxycarbonyl group, a $C_1$-$C_6$ alkylcarbonyl group or a $C_3$-$C_8$ cycloalkyl group, a $C_3$-$C_8$ cycloalkyloxy group, or a halogen atom.

6. The method of claim 1, wherein the water-dispersible particulate composition has a particle size within a range from 250 to 500 μm.

7. The method of claim 1, wherein prior to being kneaded with water, the active ingredient and surfactant are mixed and ground into powder particles having a mean particle diameter of from 1 to 20 μm.

8. The method of claim 1, wherein the active ingredient is at least one selected from the group consisting of an insecticide, a microbicide, a herbicide, and a plant growth regulator.

9. The method of claim 1, wherein the surfactant is at least one selected from the group consisting of a nonionic surfactant, an anionic surfactant, a cationic surfactant, and an ampholytic surfactant.

10. The method of claim 1, wherein in step (a) the active ingredient and the surfactant are combined with at least one additional component selected from the group consisting of a water-soluble fine powder, a mineral fine powder, an oil adsorbing fine powder, a binder, a grinding aid, and a defoaming agent.

11. The method of claim 1, wherein in step (a) the active ingredient and the surfactant are combined with at least one mineral fine powder selected from the group consisting of diatomaceous earth, clay, and calcium carbonate.

12. The method of claim 1, wherein in step (a) the active ingredient and the surfactant are combined with at least one binder selected from the group consisting of polyvinyl alcohol, carboxymethyl cellulose, and hydroxypropyl cellulose.

13. The method of claim 1, wherein in step (a) the active ingredient and the surfactant are combined with at least one grinding aid selected from the group consisting of white carbon, silica sand, and pumice.

14. The method of claim 1, wherein in step (a) the active ingredient and the surfactant are combined with at least one defoaming agent selected from the group consisting of a silicone-based surfactant, a free long-chain fatty acid and an alkali metal salt thereof.

15. The method of claim 1, wherein in step (d) the toothed rolls are arranged in parallel to the ground and the dried granules are received above into the toothed rolls.

16. The method of claim 1, wherein in step (d) the diameter of the toothed rolls is from 50 mm to 300 mm and the length thereof is from 20 mm to 1,500 mm.

17. The method of claim 1, wherein in step (d) a cross section of the irregularities on the surfaces of the toothed rolls has a profile of continuous triangular mounds.

18. The method of claim 17, wherein the height and the width (base) of the triangular mounds are each from 0.3 mm to 10 mm.

19. The method of claim 1, wherein in step (d) the distance between the toothed rolls is from 0.05 mm to 1.5 mm.

20. The method of claim 1, wherein in step (d) there is a second set of two toothed rolls which the pulverized particles subsequently pass through.

* * * * *